(12) United States Patent  
Cayre

(10) Patent No.: US 9,339,818 B2  
(45) Date of Patent: *May 17, 2016

(54) DEVICE AND METHOD FOR ISOLATING AND CULTIVATING LIVE CELLS ON A FILTER OR EXTRACTING THE GENETIC MATERIAL THEREOF

(75) Inventor: Yvon Cayre, Paris (FR)

(73) Assignee: SCREENCELL, Paris (FR)

( * ) Notice: Subject to any disclaimer, the term of this patent is extended or adjusted under 35 U.S.C. 154(b) by 1466 days.

This patent is subject to a terminal disclaimer.

(21) Appl. No.: 12/812,324

(22) PCT Filed: Jan. 8, 2009

(86) PCT No.: PCT/FR2009/000019  
§ 371 (c)(1),  
(2), (4) Date: Jul. 9, 2010

(87) PCT Pub. No.: WO2009/106760  
PCT Pub. Date: Sep. 3, 2009

(65) Prior Publication Data  
US 2011/0070642 A1    Mar. 24, 2011

(30) Foreign Application Priority Data

Jan. 9, 2008 (FR) .................................. 08 50117  
Sep. 2, 2008 (FR) .................................. 08 55878

(51) Int. Cl.  
*C12M 1/00* (2006.01)  
*C12M 3/00* (2006.01)  
(Continued)

(52) U.S. Cl.  
CPC .............. *B01L 3/5635* (2013.01); *C12M 47/04* (2013.01); *C12N 15/1017* (2013.01); *B01L 2300/0681* (2013.01); *B01L 2400/0478* (2013.01)

(58) Field of Classification Search  
CPC ................ B01L 2300/0681; B01L 2400/0478; B01L 3/5635; C12M 47/04; C12N 15/1017  
USPC ................................ 435/6.1, 29, 283.1, 308.1  
See application file for complete search history.

(56) References Cited

U.S. PATENT DOCUMENTS 3,448,011 A * 6/1969 Russomanno ............. 435/297.5  
3,920,534 A * 11/1975 Jensen et al. ................ 204/282  
(Continued)

FOREIGN PATENT DOCUMENTS

DE         198 20 178      11/1999  
DE      10 2005 008 220    8/2006  
(Continued)

OTHER PUBLICATIONS

International Search Report dated Mar. 24, 2010 from corresponding PCT application.

*Primary Examiner* — Michael Marcheschi  
*Assistant Examiner* — Shanta G Doe  
(74) *Attorney, Agent, or Firm* — Young & Thompson

(57) ABSTRACT

A device for isolating and cultivating live cells on a filter or for extracting the genetic material thereof includes: a filter holder (108) connected to a filter; a compartment (102) having an upper opening and a lower opening; and an element (110) that is mobile relative to the compartment for applying a force on the holder and releasing the holder. According to the embodiments, the filter holder is mechanically connected to the compartment or to the mobile element until the application of the force. Preferably, the device further includes a removable end piece (104) tightly and removably attached and adapted for preventing the relative movement of the mobile element and the compartment for applying the force and releasing the holder.

18 Claims, 10 Drawing Sheets

Figure 2D:
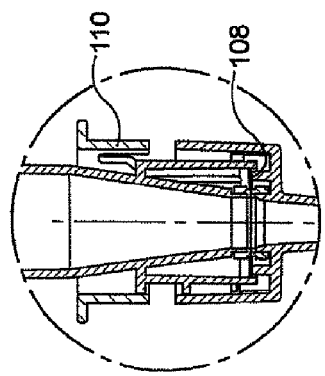

(51) Int. Cl.
  *B01L 3/00*   (2006.01)
  *C12N 15/10*  (2006.01)

(56) References Cited

U.S. PATENT DOCUMENTS

| | | | |
|---|---|---|---|
| 5,766,134 A * | 6/1998 | Lisak et al. | 600/562 |
| 6,750,039 B1 * | 6/2004 | Bargoot et al. | 435/34 |
| 8,709,786 B2 * | 4/2014 | Cayre | 435/270 |
| 2001/0032821 A1 | 10/2001 | Drocourt et al. | |
| 2007/0122809 A1 * | 5/2007 | Stevenson et al. | 435/6 |
| 2007/0134747 A1 * | 6/2007 | DiGiammarino et al. | 435/7.92 |
| 2008/0044895 A1 * | 2/2008 | Wedell et al. | 435/308.1 |

FOREIGN PATENT DOCUMENTS

| | | |
|---|---|---|
| EP | 0 463 897 | 1/1992 |
| EP | 1 455 187 | 9/2004 |
| FR | 0 503 128 | 9/1992 |
| FR | 2 801 660 | 6/2001 |
| WO | 96/37301 | 11/1996 |

\* cited by examiner

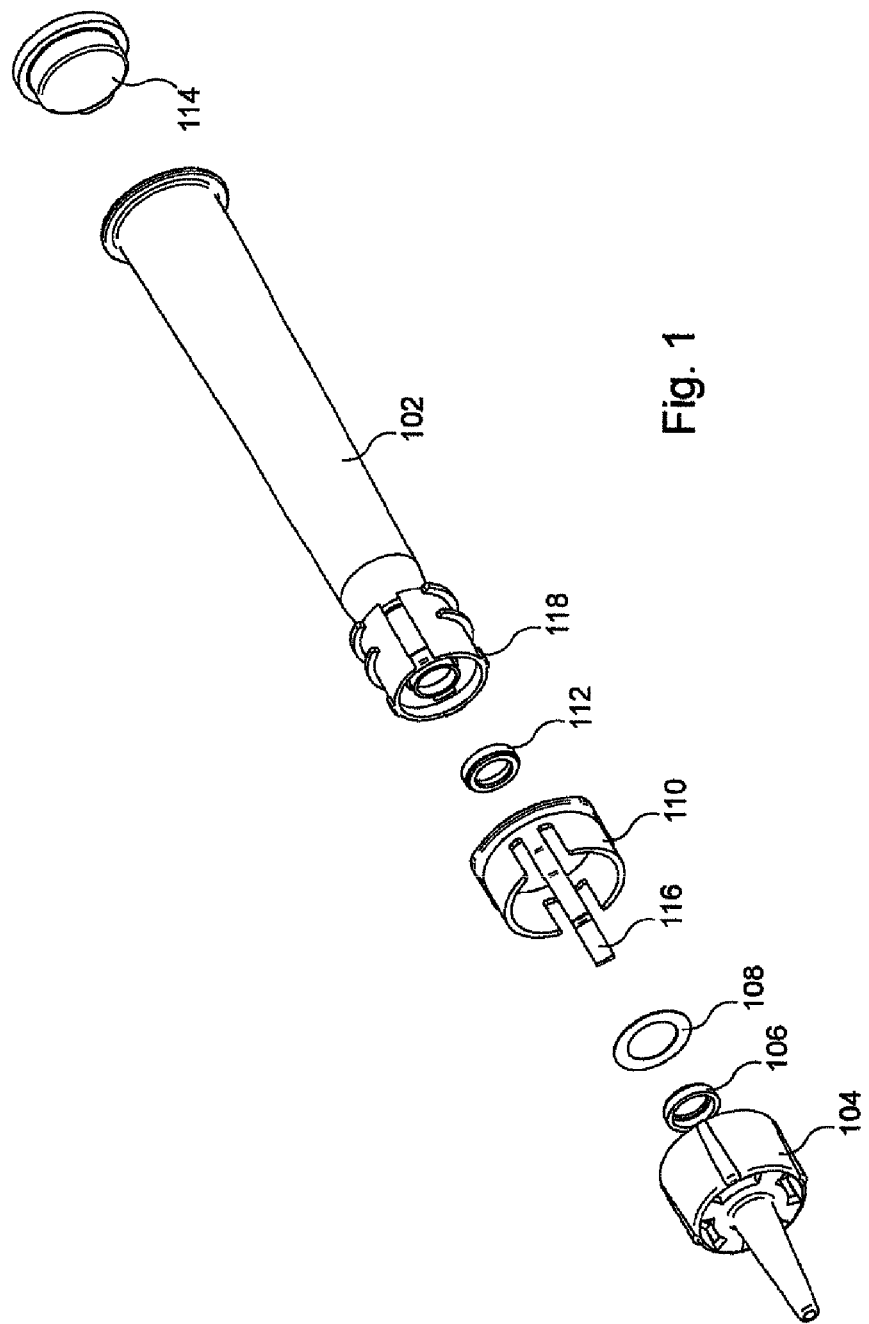

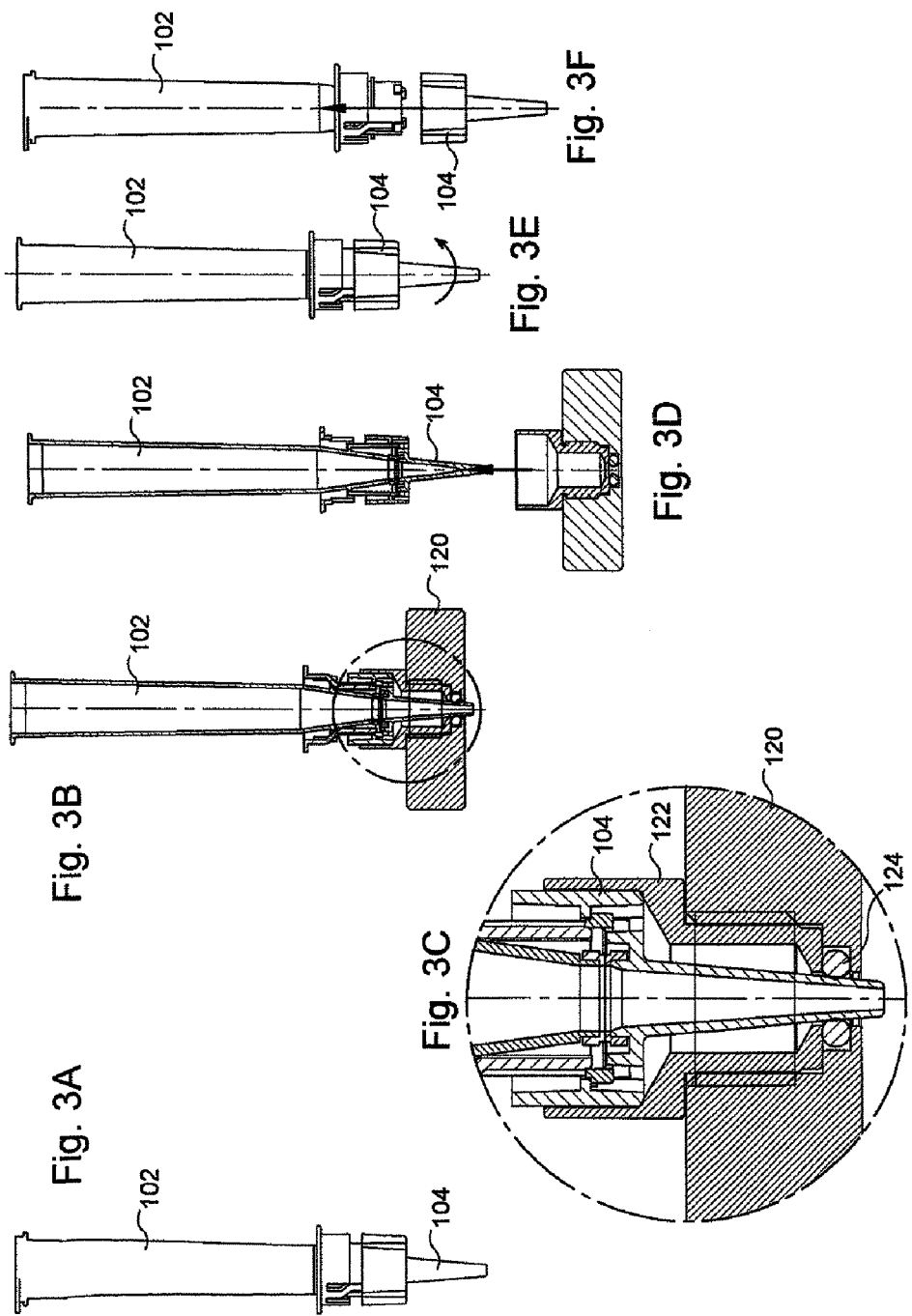

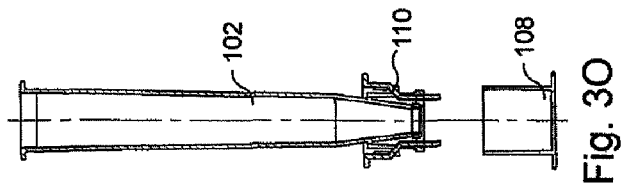
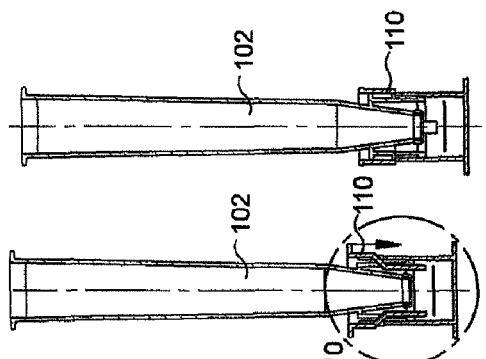
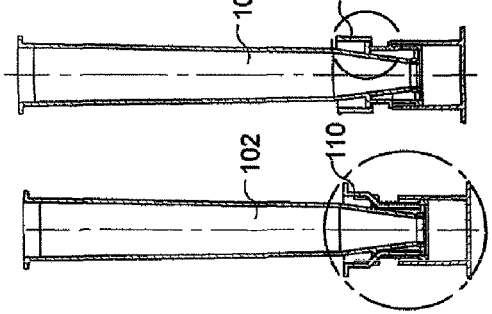
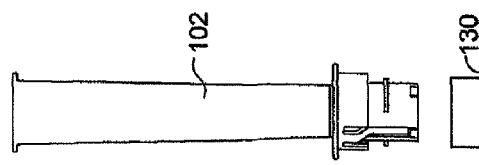
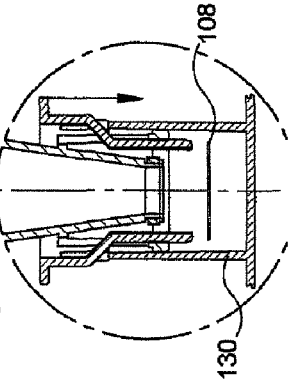
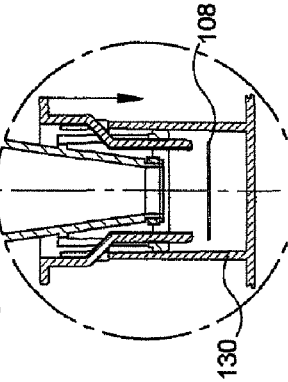
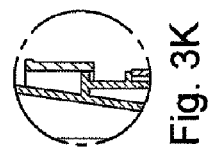
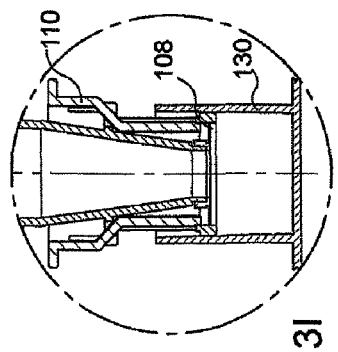

DEVICE AND METHOD FOR ISOLATING AND CULTIVATING LIVE CELLS ON A FILTER OR EXTRACTING THE GENETIC MATERIAL THEREOF

BACKGROUND OF THE INVENTION

1. Field of the Invention

The present invention concerns a device and a method for isolating and cultivating live cells on a filter or extracting amplified genetic material from live cells isolated on a filter. It applies in particular to isolating and cultivating particular cells present in a liquid, especially blood, or extracting the genetic material of those particular cells.

2. Description of the Related Art

Some particular blood cells, for example tumor cells and trophoblasts, are present in very small proportions and must be counted for a cytological analysis. However, compared to most of the other cells present in blood, they have a greater size.

It is known to apply a formaldehyde-based fixing buffer to a blood sample to fix the cells searched for and then to pass the resulting liquid into a porous filter. That filter is then used to examine the cells searched for thereon under a microscope in the laboratory. However, this procedure does not make it possible to obtain live cells.

Now, the inventor has determined that obtaining live cells would make it possible to envisage the identification of specific markers and to obtain good conditions for applying molecular biology, cytogenetic and fluorescence in situ hybridization (FISH) techniques to diagnose genetic abnormalities in tumor cells or trophoblastic cells.

The present invention aims to remedy these drawbacks and to address this requirement by making it possible, under conditions compatible with routine laboratory examination, to collect live cells that can subsequently be cultivated in appropriate media in the presence of appropriate growth factors.

The present invention also concerns extracting amplified genetic material from cells isolated on a filter and detecting mutations and levels of expression of genes coding for sensitivity and resistance to target therapies or genetic abnormalities.

It applies in particular to collecting and uniformly amplifying DNA or RNA from particular cells present in a liquid, especially blood.

It is known, for example from the document PCT/FR 2006/000562, to apply a formaldehyde-based fixing buffer to a blood sample to fix the cells searched for and then to pass the resulting liquid into a porous filter. That filter is then analyzed under a microscope in the laboratory to look for the cells. The cells can then be sampled on the filter for analysis, for example by a genetic analysis.

However, this procedure cannot be reproduced on a large scale and at a reasonable cost because of the time, equipment and precise working that it entails. Such reproduction on a large scale and at lower cost would make it possible to carry out molecular biology analyses both on tumor cells and on trophoblastic cells.

SUMMARY OF THE INVENTION

The present invention also aims to remedy these drawbacks and to address this requirement by making it possible, under conditions compatible with routine laboratory examination, to collect a large proportion of the cellular material from the cells concerned, in particular RNA and DNA, in good condition.

To this end, a first aspect of the present invention provides a device for isolating live cells on a filter or extracting their genetic material, characterized in that it includes:
   a filter support fastened to a filter,
   a compartment having an upper opening and a lower opening, and
   means mobile relative to said compartment for applying a force to the support and releasing said support.

This prevents contamination or deterioration of the live cells on the filter or the genetic material. The contents of the compartment are kept sterile during manipulation under an appropriate laminar-flow hood. Accordingly, all the steps for isolating and cultivating the cells or for extracting and analyzing their genetic material can be carried out under sterile conditions.

This device also makes it possible to recover the live cells of interest under conditions perfectly compatible with culturing them for cytomorphological and cytogenetic characterization examination. This recovery is effected directly on the filter and with virtually no loss of the cells searched for. Thus a great proportion of the cells concerned are collected at lower cost, in good condition and under conditions compatible with routine laboratory cell culture.

The device of the present invention also makes it possible to collect cellular material from particular cells quickly and efficiently, for example, after carrying out:
   a filtration step during which most of the liquid and said other cells pass through a filter the micropores of which have an intermediate diameter between that of said particular cells and that of other cells,
   a step of lysis and amplification of the DNA and/or the RNA in said compartment, and
   a step of recovering amplified genetic material from the cells on the filter that have undergone lysis.

According to particular features, the device of the present invention includes a removable end-piece removably fixed and sealed and adapted to prohibit relative movement of the mobile means and said compartment that makes it possible to apply said force and release said filter support.

Thanks to these provisions, holding of the filter-carrier in position is guaranteed. Moreover, the end-piece can protect it against splashing and contamination.

Thus the filter is retained during filtration and then released, for its recovery, by withdrawing the end-piece and imparting respective movements to the mobile means and the compartment to apply the force that releases the filter support.

According to particular features, said end-piece has a lower opening that fits onto a reduced-pressure chamber of an aspiration system.

Thanks to these provisions, cells smaller than the cells of interest, cells that have undergone lysis and most of the liquid present in the compartment can be filtered by aspiration into the reduced-pressure chamber.

According to particular features, said filter support takes the form of a washer. A washer is an annular filter-carrier.

According to particular features, said filter support is in PVC. The inventor has found that, unlike hydrophobic polyethylene, this material does not float and is more rigid than the latter material, which is beneficial for use with the filter support at the bottom of the culture well.

According to particular features, said filter support is in rigid PVC. These provisions make it possible to manipulate the filter during cytogenetic and cytomorphological analyses.

According to particular features, said filter support takes the form of an object cover slide.

According to particular features, said filter support has dimensions greater than or equal to those of an object cover slide. These provisions make it possible to mount the filter between the plate and the slide.

According to particular features, said filter support has a thickness less than or equal to 0.4 mm and preferably 0.3 mm.

Thanks to these provisions, the filter support may be used under a microscope, even at high magnification, with no risk of touching any part of the microscope during lateral displacement of the filter support.

According to particular features, said filter support takes the form of at least part of an Eppendorf tube.

According to particular features, the upper interior part of said filter support reproduces the shape of the upper interior part of an Eppendorf tube.

Thanks to these provisions, the top opening of said filter support may be closed with an Eppendorf tube stopper.

According to particular features, the lower interior part of said filter support reproduces the shape of the lower interior part of an Eppendorf tube.

According to particular features, said filter has a diameter less than or equal to 5 mm and preferably 3.5 mm, which is beneficial for lysis of the cells and preamplification of the genetic material.

Thus the lower interior surface of an Eppendorf tube can be simulated.

According to particular features, the upper exterior part of said filter support reproduces the shape of the upper interior part of an Eppendorf tube.

Thanks to these provisions, the filter support can be inserted into the upper part of an Eppendorf tube.

Thus a seal can be created between the upper exterior part of said filter support and the upper interior part of an Eppendorf tube.

Thanks to the last three of the above provisions, the filter support has a column function.

According to particular features, the filter support includes polycarbonate.

Thanks to these provisions, the pores of the filter retain the lysis buffer and the reagents to amplify the genetic material.

According to particular features, the filter support is mechanically connected to said compartment up to application of said force.

According to particular features, said filter support is mechanically connected to said mobile means up to application of said force.

A second aspect of the present invention provides a method for isolating live cells on a filter or extracting their genetic material, characterized in that it includes:
- a step of fastening a filter support fastened to a filter to a compartment having an upper opening and a lower opening or to means mobile relative to said compartment, and
- a step of moving said mobile means and said compartment to apply a force to the filter support and release said filter support.

According to particular features, during the movement step, the filter support is passed directly to a culture well.

This prevents any contamination or deterioration of the live cells on the filter or of the extracted genetic material. Thanks to each of these provisions, the content of the compartment remains sterile during manipulation under a laminar-flow hood. Thus all the steps are effected under sterile conditions appropriate to cell culture or genetic material extraction.

The advantages, objects and particular features of the above method being similar to those of the device of the present invention, as succinctly set out above, they are not repeated here.

Thus the method of the present invention makes it possible to collect cellular material quickly and efficiently. The cellular material recovered using the present invention is generally the genetic material of the cells. Thus the method of the present invention makes it possible to recover genetic material from rare cells, even a single isolated cell, directly from the filter and practically without losses. Thus a large proportion of the genetic material of the cells concerned is collected in good condition under conditions compatible with routine laboratory examination.

According to particular features, the method of the present invention, as succinctly described above, includes, after the lysis step, a step of amplification of the DNA and/or the RNA and, during the recovery step, the amplified genetic material is recovered from the cells that have undergone lysis.

According to particular features, uniform amplification preserving the quantitative aspect of the DNA and RNA is effected during the lysis and amplification step.

According to particular features, the method of the present invention, as succinctly described above, further includes a detection step during which the amplified DNA is used as a matrix for detecting at least one mutation of a gene coding for sensitivity or resistance to at least one target therapy.

According to particular features, the method of the present invention, as succinctly described above, further includes a detection step during which the amplified DNA is used as a matrix for detecting a variation of the level of expression of a gene coding for sensitivity or resistance to the target therapies.

According to particular features, the method of the present invention, as succinctly described above, further includes a detection step during which RNA is converted into cDNA and said cDNA is used to detect the level of expression of a gene coding for sensitivity or resistance to the target therapies.

According to particular features, a quantitative and real-time polymerase chain reaction (PCR) is effected during the detection step.

According to particular features, during the detection step, at least one pair of forward and reverse primers is used to amplify a predetermined sequence of interest.

According to particular features, during the detection step, at least one pair of probes is used.

According to particular features, at least two probes of a pair of probes are coupled to different fluorochromes and are defined so that one recognizes the mutated sequence and the other recognizes the normal sequence.

According to particular features, at least one pair of primers and one pair of probes are adapted to detect the G12D mutation of the K-ras gene coding for resistance to Erlotinib and Gefitinib.

According to particular features, at least one primer includes at least 80% of the sequence AGGCCTGCTGAAAATGACTGAATAT (SEQ ID NO: 1).

According to particular features, at least one primer includes at least 80% of the sequence TCGTCCACAAAATGATTCTGAATTAGCT (SEQ ID NO: 2).

According to particular features, at least one probe includes at least 80% of the sequence TTGGAGCTGGTGGCGT (SEQ ID NO: 3).

According to particular features, at least one probe includes at least 80% of the sequence TGGAGCTGATGGCGT (SEQ ID NO: 4).

According to particular features, at least one pair of primers and one pair of probes are adapted to detect the G12V mutation of the K-ras gene coding for resistance to Erlotinib and Gefitinib.

According to particular features, at least one primer includes at least 80% of the sequence AGGCCTGCT-GAAAATGACTGAATAT (SEQ ID NO: 5).

According to particular features, at least one primer includes at least 80% of the sequence TCGTCCACAAAAT-GATTCTGAATTAGCT (SEQ ID NO: 6).

According to particular features, at least one probe includes at least 80% of the sequence TTGGAGCTGGTG-GCGT (SEQ ID NO: 7).

According to particular features, at least one probe includes at least 80% of the sequence TTGGAGCTGTTG-GCGT (SEQ ID NO: 8).

According to particular features, at least one pair of primers and one pair of probes are adapted to detect the G13C mutation of the K-ras gene coding for resistance to Erlotinib and Gefitinib.

According to particular features, at least one primer includes at least 80% of the sequence AGGCCTGCT-GAAAATGACTGAATAT (SEQ ID NO: 9).

According to particular features, at least one primer includes at least 80% of the sequence TCGTCCACAAAAT-GATTCTGAATTAGCT (SEQ ID NO: 10).

According to particular features, at least one probe includes at least 80% of the sequence TTGGAGCTGGTG-GCGT (SEQ ID NO: 11).

According to particular features, at least one probe includes at least 80% of the sequence TTGGAGCTGGT-TGCGT (SEQ ID NO: 12).

According to particular features, at least one pair of primers and one pair of probes are adapted to detect the L858R mutation of the EGFR gene coding for increased sensitivity to Erlotinib and Gefitinib.

According to particular features, at least one primer includes at least 80% of the sequence GCAGCATGTCAA-GATCACAGATTT (SEQ ID NO: 13).

According to particular features, at least one primer includes at least 80% of the sequence CCTCCTTCTGCATG-GTATTCTTTCT (SEQ ID NO: 14).

According to particular features, at least one probe includes at least 80% of the sequence CAGTTTGGCCAGC-CCA (SEQ ID NO: 15).

According to particular features, at least one probe includes at least 80% of the sequence CAGTTTGGCCCGC-CCA (SEQ ID NO: 16).

A third aspect of the present invention provides a device for isolating live cells on a filter, characterized in that it includes:
   a filter support fastened to a filter,
   a compartment having an upper opening and a lower opening adapted to retain said support and said filter, and
   means for applying a force to the support from inside the compartment.

This device makes it possible to recover live cells of interest under conditions perfectly compatible with culturing them for genetic examination.

According to particular features, the device of the present invention, as succinctly described above, includes, in the compartment, a mobile part adapted to bear on the filter support and to receive a force exerted by a piston inserted in the compartment.

According to particular features, the device of the present invention, as succinctly described above, includes, at its lower opening, an end-piece for retaining the filter and the filter support, said end-piece being removably fixed and sealed to the compartment.

Thanks to these features, the filter is retained during filtration and then released, for recovery, by withdrawing the end-piece and applying a force to the filter support from inside the compartment.

According to particular features, said end-piece has a lower opening that is fitted to a reduced-pressure chamber.

Thanks to these features, cells smaller than the cells of interest, cells that have undergone lysis and most of the liquid present in the compartment can be filtered by aspiration into the reduced-pressure chamber.

A fourth aspect of the present invention provides a method for collecting cells present in a liquid, characterized in that it includes:
   a step of fastening a filter support to a compartment having an upper opening and a lower opening adapted to retain said support and said filter inside said compartment,
   a step of filtering a liquid containing live cells through said filter, and
   a step of applying a force to the support from inside the compartment to recover the filter outside the compartment.

The particular advantages, objects and features of this method being similar to those of the device of the third aspect of the present invention, as succinctly described above, they are not repeated here.

A fifth aspect of the present invention provides a method for isolating live cells on a filter, characterized in that it includes:
   a step of inserting a liquid containing said cells and a filtration buffer with no fixative into a compartment via an upper opening of the compartment, said compartment having a lower opening, a filter being positioned between the two openings the micropores of which have an intermediate diameter between that of said particular cells and that of other cells,
   a filtration step during which most of the liquid and said other cells pass through the filter, and
   a step of recovering the filter and the cells remaining on the filter.

This method makes it possible to recover the live cells of interest under conditions perfectly compatible with culturing them for genetic examination. This recovery is effected directly on the filter and with virtually no loss of the cells searched for. Thus a large proportion of the cells concerned is recovered in good condition under conditions compatible with routine laboratory cell culture.

According to particular features, the method as succinctly described above includes, prior to the filtration step, a step of applying to the liquid containing the particular cells a filtration buffer with no fixative consisting of a culture medium and a lysis agent.

According to particular features, during the filtration step, aspiration is applied below the filter by a pressure reduction less than or equal to 25 mBar.

Thanks to these provisions, filtration is efficient and fast and does not damage the live cells to be recovered on the filter.

According to particular features, during the filtration step, an end-piece of the compartment retains the filter in the compartment and, during the step of recovering the filter, said end-piece is withdrawn from the compartment, a piston is introduced into the compartment and said piston applies a force to a support of said filter.

This force makes it possible to extract from the compartment the support carrying the filter at the lower end of the compartment and thus the filter itself. Moreover no force being exerted directly on the filter and the applied force causing no pressure rise, the cells carried by the filter are not damaged during recovery of the filter.

According to particular features, during the recovery step, the filter is passed directly from the compartment to a culture well plate and/or a culture flask.

This prevents any contamination or deterioration of the live cells on the filter. Thanks to each of these provisions, the content of the compartment remains sterile during manipulation under a laminar-flow hood making it possible to manipulate the cells under sterile conditions. Thus all the steps are effected under sterile conditions appropriate to cell culture.

A sixth aspect of the present invention provides a device for collecting cells present in a liquid, characterized in that it includes:

means for inserting the liquid and a filtration buffer with no fixative into a compartment via an upper opening of the compartment, said compartment having a lower opening, a filter positioned between the two openings of the compartment, said filter having micropores with an intermediate diameter between that of said particular cells and that of other cells, filter means for passing most of the liquid and said other cells through a filter, and means for recovering the filter and cells remaining on the filter.

The particular advantages, objects and features of this device being similar to those of the method of the fifth aspect of the present invention, as succinctly described above, they are not repeated here.

BRIEF DESCRIPTION OF THE DRAWING FIGURES

Figure 4:
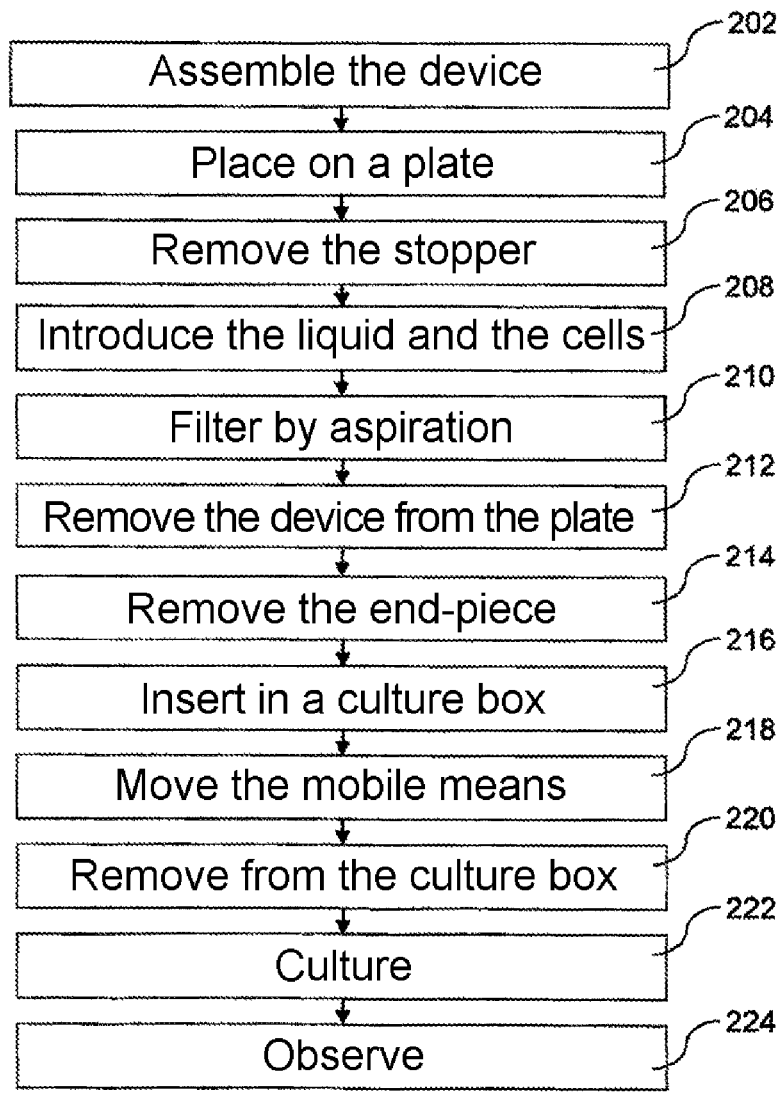
Figure 5:
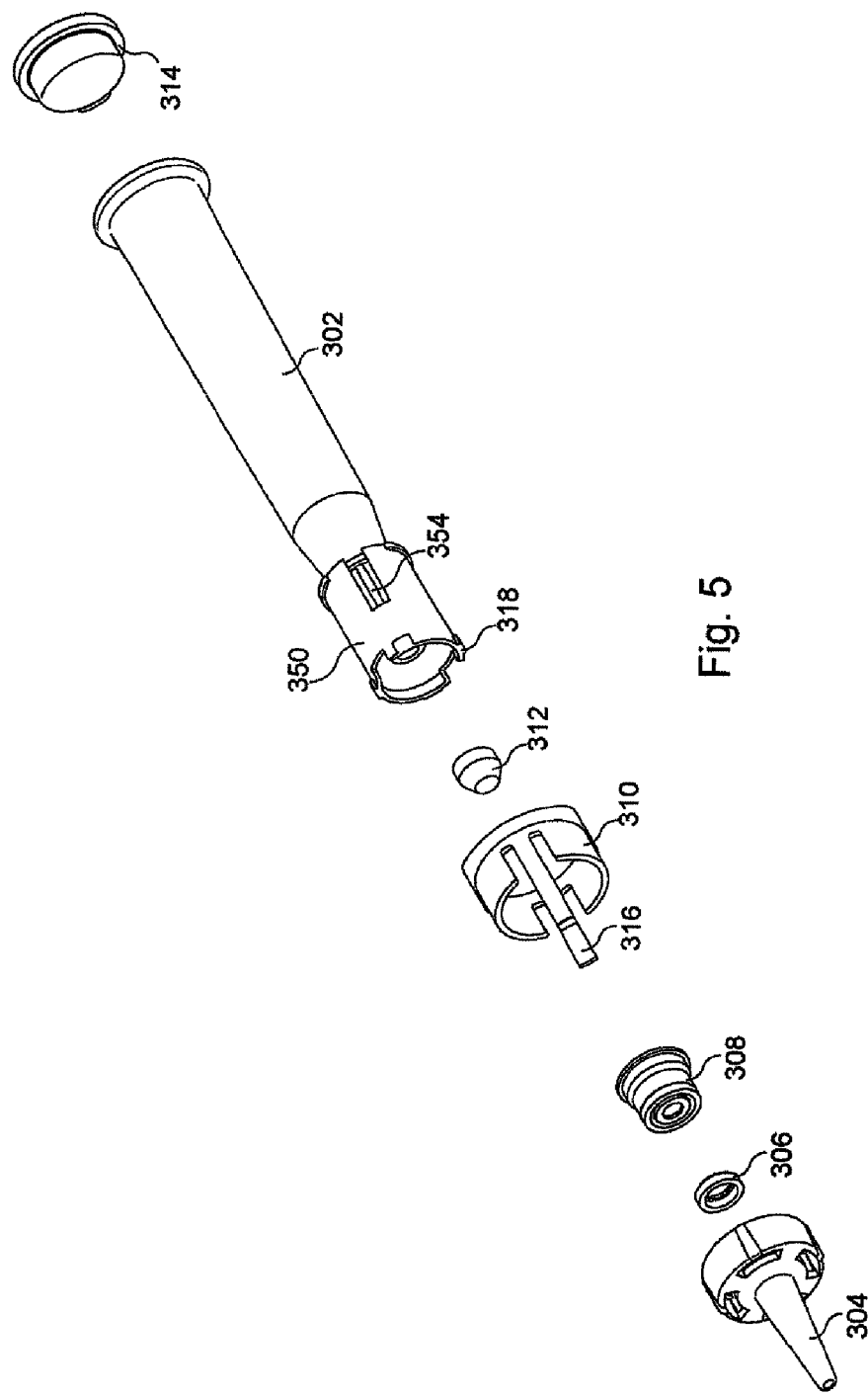
Figure 6:
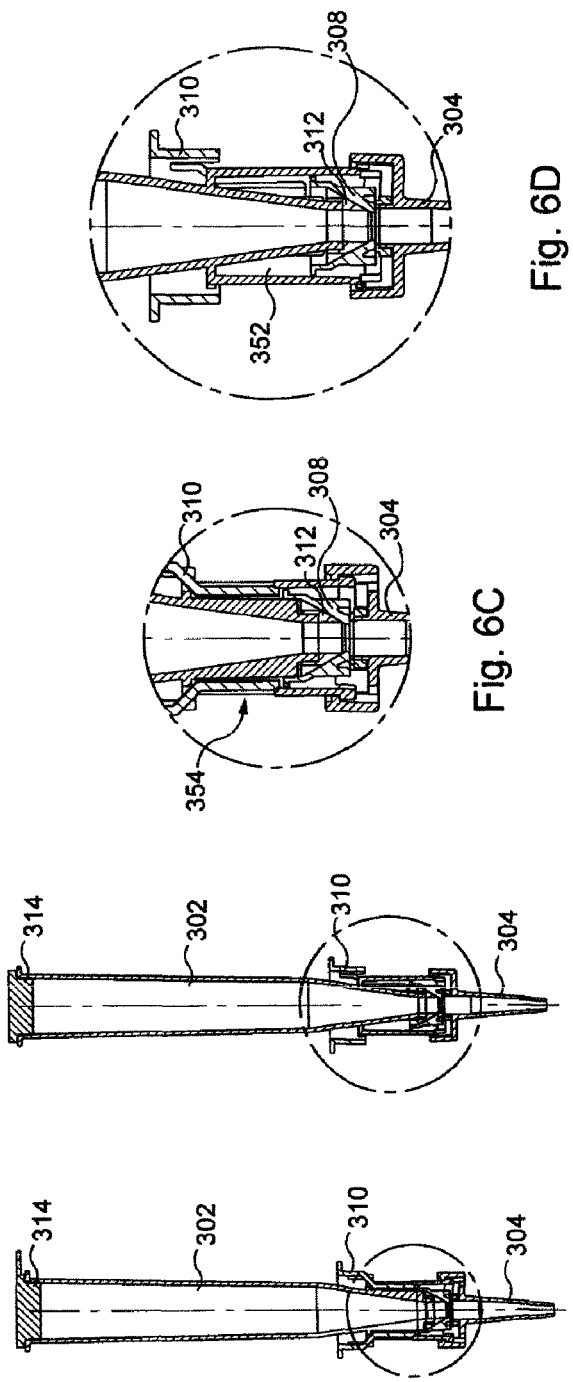
Figure 7:
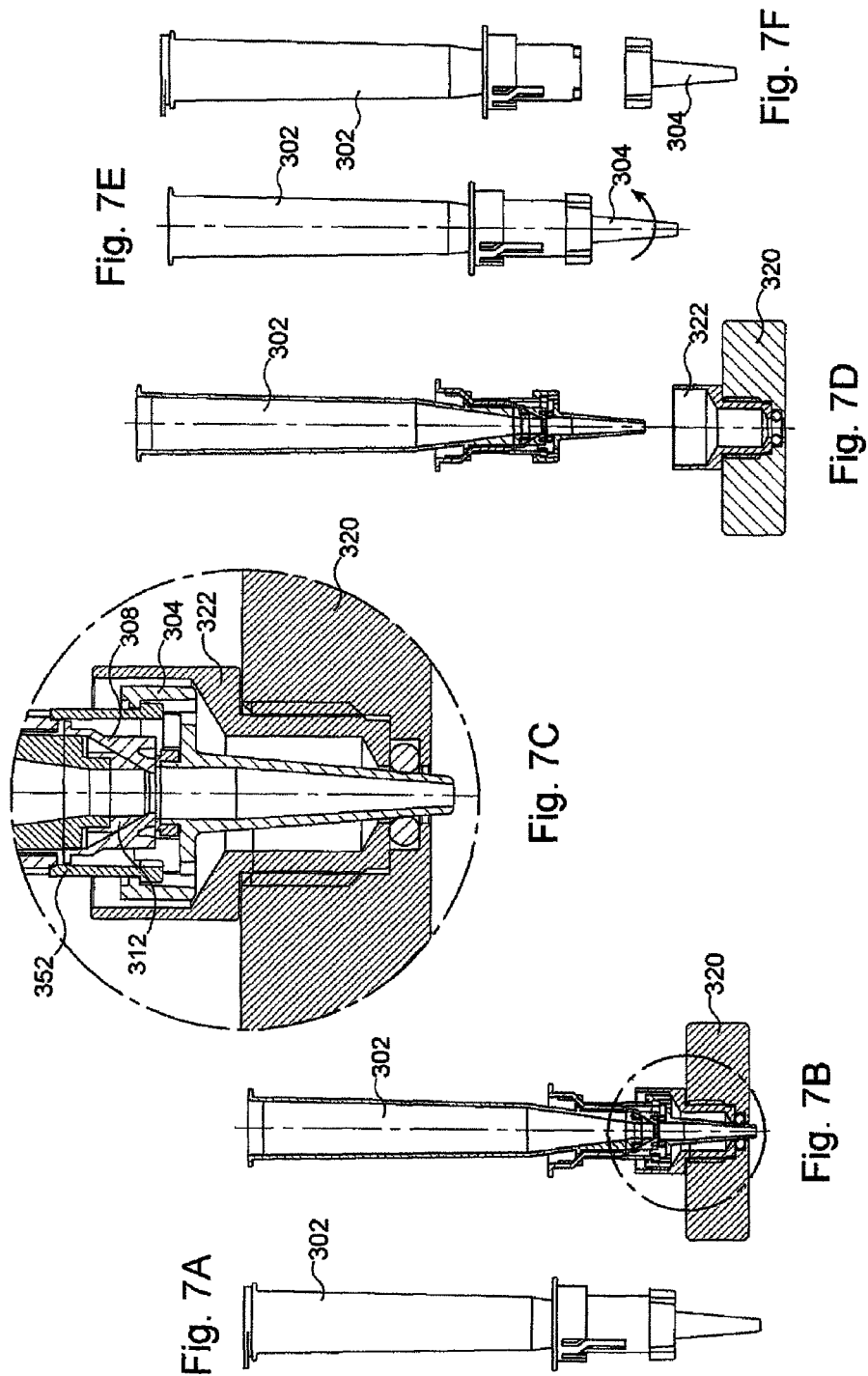
Figure 8:
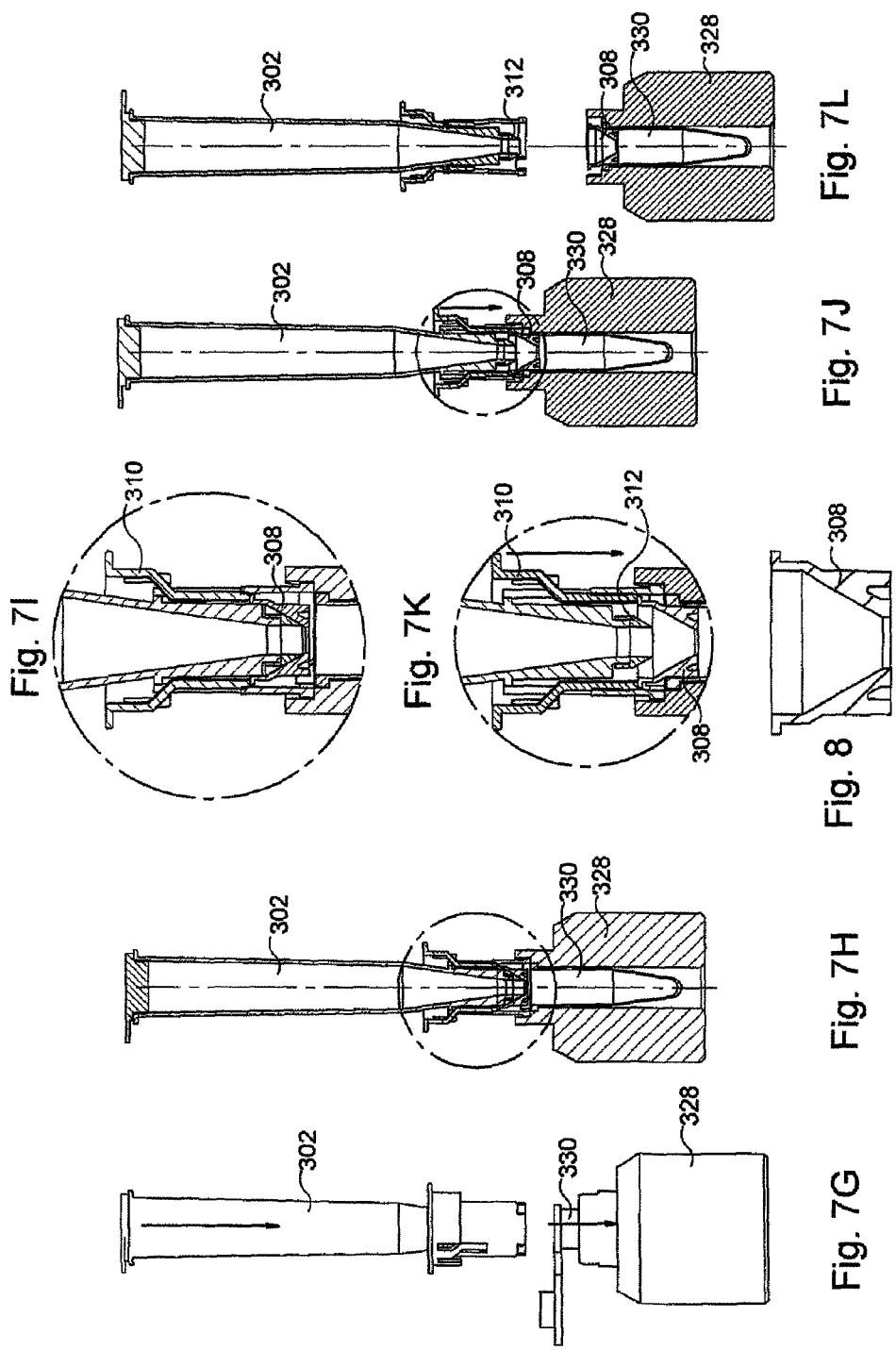
Figure 9:
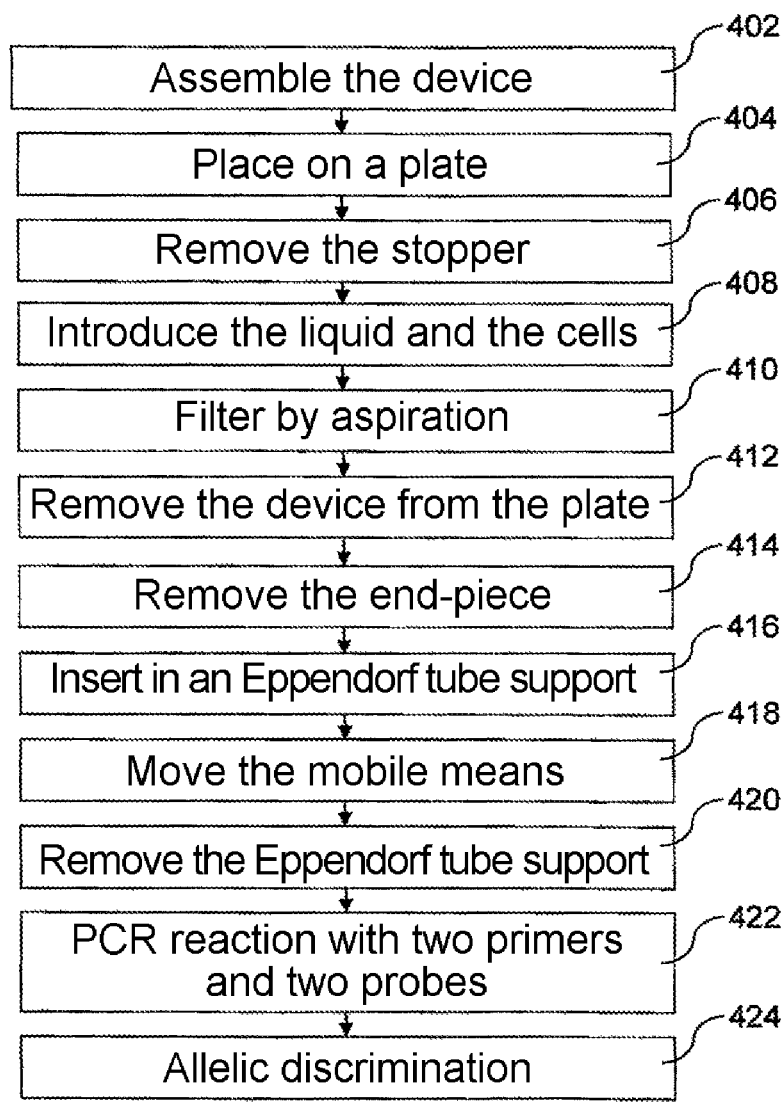

Other advantages, objects and features of the present invention will emerge from the following description given by way of nonlimiting explanation with reference to the appended figures, in which:

FIG. 1 represents, diagrammatically and in perspective, the assembly of the parts of the device of a first embodiment of the present invention, FIGS. 2A to 2D represent, diagrammatically and in mutually perpendicular axial sections, the device of the first embodiment before use, FIGS. 3A to 3O represent, diagrammatically, in elevation or in section, steps of the use of the device of the first embodiment of the present invention, FIG. 4 represents, in flowchart form, steps executed in the method of a first particular embodiment of the present invention, FIG. 5 represents, diagrammatically and in perspective, the assembly of the parts of the device of a second particular embodiment of the present invention, FIGS. 6A to 6D represent, diagrammatically and in mutually perpendicular axial sections, the device of the second embodiment prior to use, FIGS. 7A to 7L represent, diagrammatically, in elevation or in section, steps of using the device of the second embodiment of the present invention, FIG. 8 represents, in section, a filter support integrated into the device of the second embodiment of the present invention, and FIG. 9 represents, in flowchart form, steps executed in the method of a second particular embodiment of the present invention.

There are seen in FIG. 1 a reservoir or compartment 102, an end-piece 104, a seal 106, a filter support 108, mobile means 110, a seal 112 and a stopper 114.

DETAILED DESCRIPTION OF THE INVENTION

The general shape of the compartment 102 is cylindrical. Its upper end may be closed and sealed by the stopper 114. The lower end of the compartment 102 has, on its external surface, discontinuous rings the discontinuities whereof guide lugs of the mobile means 110, said rings guiding the body of the mobile means 110.

The mobile means 110 have a cylindrical general shape with two lugs 116 extending toward the end-piece 104 and coming closer together in that direction so as to be separated from each other by a distance less than the diameter of the filter support 108. As will emerge hereinafter, this particular shape, notably that of the lugs 116 that curve toward each other, enables the mobile means 110, after withdrawal of the end-piece 104, to push the filter support 108 in order to release it from the compartment 102 on movement of the mobile means toward the filter support 108.

The ends of the lugs 116 of the mobile means 110 and the lower end of the compartment 102 are adapted to enter a culture box or well. On the other hand, the discontinuous ring at the end of the compartment 102 has a diameter such that it bears on the edge of the culture box or well.

An end-piece or adapter 104 that grips the exterior wall of the compartment 102 and has a tapered lower opening of smaller diameter than the compartment 102 is placed at the lower opening of the compartment 102 in a sealed, sterile and removable fashion.

This tapered lower opening of the end-piece or adapter 104 has a length sufficient to prevent potential contamination of the end of the compartment 102 by splashes coming from a chamber in which the pressure is reduced.

In a manner coordinated with the shape of the lower end of the compartment 102, which has lateral lugs 118, the end-piece 104 has rotation locking means for gripping said lugs in a manner known in itself. Thus the end-piece 104 guarantees that the filter-holder is held in position during the filtration steps. The end-piece 104 also protects the filter from splashing and contamination.

The lower end of the compartment 102 has an opening which, after fitting, discharges onto the filter carried by the filter support 108 which is itself held in position on the one hand by the lower end of the compartment 102 and on the other hand by the end-piece 104.

In the first embodiment, the filter support 108 takes the form of an annular washer. The microperforated filter is welded under the filter support 108 and then inserted with it into the lower end of the compartment 102.

The filter support 108 is preferably in PVC and has a thickness less than or equal to 0.4 mm and preferably less than 0.3 mm. Its outside diameter is 12.6 mm, for example. The diameter of the filter carried by the filter support 108 is 8.2 mm, for example.

The compartment 102, the end-piece 104 and the mobile means 110 are produced in polypropylene, for example. The seals 106 and 112 are in silicone, for example.

Figure 2B:
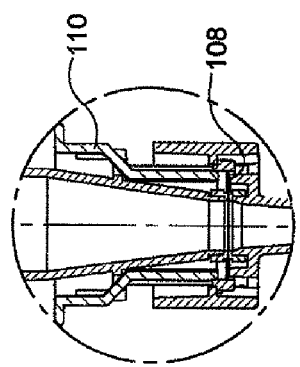
Figure 2C:
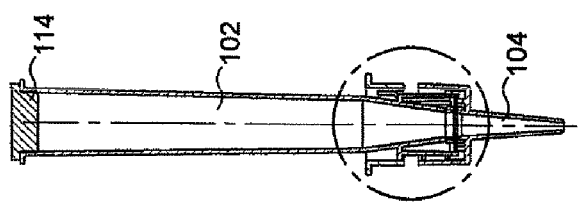
Figure 2A:
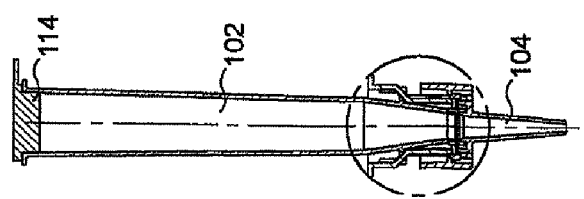

FIGS. 2A and 2C are mutually perpendicular axial sections of the device of the first embodiment of the present invention when the parts shown in FIG. 1 have been assembled. FIGS. 2B and 2D are enlarged detail views of parts of FIGS. 2A and 2C, respectively. The elements described with reference to FIG. 1 appear in FIGS. 2A to 2D.

FIG. 3A represents the device in elevation in its storage configuration. FIG. 3B represents the placement of the device on a plate 120 of a known type aspiration system (not shown) after removal of the stopper 114 and introduction of liquid (not shown), for example blood, into the compartment 102 through its upper opening. FIG. 3C is an enlarged detail view of part of FIG. 3B. It is seen in FIGS. 3B and 3C that the end-piece 104 is held in position in a part 122 and that an O-ring 124 seals the connection between the interior of the end-piece and thus, via the filter 108, the interior of the compartment 102 and the aspiration chamber of the aspiration system. It is seen that the end-piece 104 projects into the interior of the aspiration chamber.

During aspiration, some particular cells of larger diameter in the liquid present in the compartment 102 are retained by the filter whereas most of the liquid, the contents and walls of cells that have undergone lysis and cells with smaller dimensions than the cells to be collected are aspirated out of the compartment 102 through the filter.

As shown in FIG. 3D, after filtration, the device is removed from the plate. Then, as shown in FIGS. 3E and 3F, the end-piece 104 is removed after rotating it to release the lugs 118. Then, as shown in FIGS. 3G and 3H, the end of the compartment 102 is inserted into a culture box or well 130.

As disclosed above and as shown in FIG. 3I, the close together ends of the lugs 116 of the mobile means 110 and the lower end of the compartment 102 are adapted to penetrate into a culture box or well. On the other hand, the discontinuous ring at the end of the compartment 102 has a diameter such that it bears on the edge of the culture box or well 130.

To be more precise, as shown in FIGS. 3J and 3K, in this position the mobile means 110 are still able to move parallel to the axis of the compartment 102.

As shown in FIGS. 3N and 3M, during this movement, the lugs 116 of the mobile means when moved by the fingers of an operator exert a vertical downward force on the filter support 108 and release it from the lower end of the compartment 102. The filter support 108 then drops into the culture box or well 130.

Finally, as shown in FIG. 3O, the compartment 102 and the mobile means 110 are removed from the culture box or well 130.

FIG. 4 summarizes the above steps.

During a step 202, the parts of the device are assembled. During a step 204, the device is placed on a plate 120 of an aspiration system. During a step 206, the stopper 114 is removed. During a step 208, a liquid, for example blood, containing cells to be cultivated is introduced via the upper end of the compartment 102.

During a step 210, cells smaller than the cells of interest, cells that have undergone lysis and most of the liquid present in the compartment 102 are filtered by aspirating them into the reduced-pressure chamber of the aspiration system.

During a step 212, the device is removed from the plate. During a step 214, the end-piece 104 is removed. During a step 216, the end of the compartment 102 is inserted into a culture box or well.

During a step 218, the mobile means and the compartment are moved to exert a force on the filter support and release it in order for it to drop into the culture box or well. During a step 220 the compartment 102 and the mobile means 110 are removed from the culture box or well 130.

During a step 220, cell culture takes place in the culture well 130 in a manner known in the art. Note that the presence of the support 108 around the upper face of the filter, which carries the cells isolated on the filter, makes it possible to prevent the cells leaving the filter.

During the step of culturing the live cells of interest on the filter, the filter is for example covered with a thin layer of Matrigel (Registered Trade Mark) (or brought into contact with a layer of Matrigel previously placed on the bottom of the plate well and/or culture flask on which it rests) containing factors appropriate to the growth of the cells of interest.

When it is required to observe the cells, or their genetic material, during a step 222, the filter support 108 is picked up with tweezers, which is facilitated by the presence of lateral cylindrical holes or notches in the upper face of the filter support 108.

The filter support 108 may then be placed on a glass plate and a disc-shaped glass slide placed on the filter that has a diameter matching the free upper surface of the filter. The analysis of the cells or of their genetic material is then effected in a manner known in itself.

There are seen in FIG. 5 a reservoir or compartment 302, an end-piece 304, a seal 306, a filter support 308, mobile means 310, a seal 312 and a stopper 314.

The general shape of the compartment 302 is cylindrical. Its upper end may be blocked and sealed by the stopper 314. The lower end of the compartment 302 has, on its external face, a cylinder 350 separated from the body of the compartment 302 except for mechanical connections in the form of lateral ribs 352. This cylinder 350 has an outside diameter that corresponds to the inside diameter of the body of the mobile means 310 in order to guide it as it moves. The cylinder 350 is provided with openings 354 adapted to allow the lugs 316 of the mobile means 310 to enter and slide longitudinally.

The mobile means 310 have a cylindrical general shape with two lugs 316 extending toward the end-piece 304 and coming closer together in this direction so as to be separated from each other by a distance less than the diameter of the filter support 308. As explained later, this particular shape, in particular that of the lugs 316 that are curved toward each other, enables the mobile means 310, following removal of the end-piece 304, to push on the filter support 308 in order to release it from the compartment 302 during movement of the mobile means toward the filter support 308.

In a manner coordinated with the shape of the lower end of the compartment 302, which has lateral lugs 318, the end-piece 304 has rotation locking means for gripping said lugs in a manner known in itself. Thus the end-piece 304 guarantees that the filter-holder is held in position during the filtration steps. The end-piece 304 also protects the filter from splashing and contamination.

The lower end of the compartment 302 has an opening which, after fitting, discharges onto the filter carried by the filter support 308 which is itself held in position on the one hand by the lower end of the compartment 302 and on the other hand by the end-piece 304.

As shown in FIG. 8, in the second embodiment, the filter support 308 has a shape coordinated with that of an Eppendorf tube.

In particular:
the interior upper part of the support 308 has the shape of the interior upper part of an Eppendorf tube, which makes it possible to close the upper opening of said support with an Eppendorf tube stopper,
the interior lower part of the support 308 has the shape of the interior lower part of an Eppendorf tube, which makes it possible to simulate an interior lower surface of an Eppendorf tube, and
the exterior lower part of the support 308 has the shape of the interior upper part of an Eppendorf tube, which makes it possible to insert the filter support 308 into the upper part of an Eppendorf tube.

Moreover, the filter support 308 has a column function to enable lysis of cells retained on the filter and transfer of cellular lysate and genetic material from the filter support to the Eppendorf tube.

The filter support 308 is preferably in PC (polycarbonate). The compartment 302, the end-piece 304 and the mobile means 310 are produced in polypropylene, for example. The seals 306 and 312 are in silicone, for example.

FIGS. 6A and 6C are mutually perpendicular axial sections of the device of the first embodiment of the present invention when the parts shown in FIG. 5 have been assembled. FIGS. 6B and 6D are enlarged detail views of parts of FIGS. 6A and 6C, respectively. The elements described with reference to FIG. 5 are seen in FIGS. 6A to 6D.

FIG. 7A represents the device in elevation in its storage configuration. FIG. 7B represents the placement of the device on a plate 320 of a known type aspiration system (not shown) after removal of the stopper 314 and introduction of liquid (not shown), for example blood, into the compartment 302 through its upper opening. FIG. 7C is an enlarged detail view of part of FIG. 7B. It is seen in FIGS. 7B and 7C that the end-piece 304 is held in position in a part 322 and that an O-ring 324 seals the connection between the interior of the end-piece and thus, via the filter 308, the interior of the compartment 302 and the aspiration chamber of the aspiration system. It is seen that the end-piece 304 projects into the interior of aspiration chamber.

Thus cells smaller than the cells of interest, cells that have undergone lysis and most of the liquid present in the compartment 302 are filtered by aspirating them into the reduced-pressure chamber.

As shown in FIG. 7D, after filtration, the device is removed from the plate. Then, as shown in FIGS. 7E and 7F, the end-piece 304 is removed after rotating it to release the lugs 318. Then, as shown in FIGS. 7G, 7H and 7I, the end of the compartment 302 is inserted into an Eppendorf tube support 328 provided with an Eppendorf tube 330.

As shown in FIGS. 7J and 7K, the mobile means 310 are then moved downward, parallel to the axis of the compartment 302. During this movement, the lugs 316 of the mobile means 310 when moved by the fingers of an operator exert a vertical downward force on the filter support 308 and release it from the lower end of the compartment 302. The filter support 308 then drops into the Eppendorf tube 330.

Finally, as shown in FIG. 7L, the compartment 302 and the mobile means 310 are removed.

FIG. 9 summarizes the above steps.

During a step 402, the parts of the device are assembled. During a step 404, the device is placed on a plate 320 of an aspiration system of known type (not shown). During a step 406, the stopper 314 is removed. During a step 408, a liquid, for example blood, containing cells to be cultivated is introduced via the upper end of the compartment 302.

During a step 410, cells smaller than the cells of interest, cells that have undergone lysis and most of the liquid present in the compartment 302 are filtered by aspirating them into the reduced-pressure chamber.

During a step 412, the device is removed from the plate. During a step 414, the end-piece 304 is removed. During a step 416, the end of the compartment 302 is inserted in an Eppendorf tube support.

Then, during a step 418, the mobile means and the compartment are moved to exert a force on the filter support and release it in order for it to drop into the Eppendorf tube. Finally, during a step 420, the compartment 302 and the mobile means 310 are removed and the stopper of the Eppendorf tube is closed.

The Eppendorf tube is then used in the manner known in itself, for example with steps of lysis, centrifuging and recovery of genetic material with pre-amplification of the global genome.

During steps 422 and 424, an analysis is effected of the genetic material, in particular the DNA or RNA of the cells searched for, collected in these tubes 125 or 126. The amplified DNA is used as a matrix to detect mutations of sensitivity or resistance to the target therapies. Also, or instead, the complementary DNA (cDNA) produced from the RNA by RT conversion and amplified is used as a matrix to detect the level of expression of genes coding for sensitivity or resistance to the target therapies.

A defined volume of the amplified genetic material, in particular the DNA, is sampled to detect the mutations in sensitivity or resistance to the target therapies using pairs of forward and reverse primers and pairs of probes during a quantitative and real-time polymerase chain reaction (PCR).

The principle of searching for mutations in sensitivity or resistance to the target therapies employed in the embodiment shown is as follows. Single nucleotide polymorphism (SNP) genotyping assay or allelic discrimination provides information as to the presence or absence of a one-off mutation in a gene. The first step 422 of allelic discrimination is a real-time quantitative PCR performed with two primers to amplify the sequence of interest and two probes, for example TaqMan (Registered Trade Mark) probes. One of the probes recognizes the mutated sequence and the other recognizes the normal sequence. The two probes are associated with different fluorochromes, for example VIC for the probe hybridizing with the normal sequence and FAM for the probe hybridizing with the mutated sequence. The second step 424 calls on an allelic discrimination program measuring the initial fluorescence and the final fluorescence emitted by the FAM and/or VIC fluorochromes. This program makes it possible to distinguish between the various sequences present in each sample:

an increase of only the VIC fluorescence indicates a homozygote profile for the normal sequence, an increase of only the FAM fluorescence indicates a homozygote profile for the mutated sequence, an increase of both the VIC and FAM fluorescence indicates a heterozygote profile.

To detect mutations, the following sequences of primers and probes (forward and reverse, 5' to 3') are used, for example:

For the G12D mutation of the K-ras gene coding for resistance to Erlotinib and Gefitinib:

```
                                           (SEQ ID NO: 1)
   forward primer AGGCCTGCTGAAAATGACTGAATAT, (SEQ ID NO: 2)
   reverse primer TCGTCCACAAAATGATTCTGAATTAGCT, (SEQ ID NO: 3)
   native probes, color VIC TTGGAGCTGGTGGCGT, (SEQ ID NO: 4)
   mutated probe, color FAM TGGAGCTGATGGCGT.
```

For the G12V mutation (coding 12) of the K-ras gene coding for resistance to Erlotinib and Gefitinib:

```
                                           (SEQ ID NO: 5)
   forward primer AGGCCTGCTGAAAATGACTGAATAT,
```

```
                                        (SEQ ID NO: 6)
reverse primer TCGTCCACAAAATGATTCTGAATTAGCT, (SEQ ID NO: 7)
native probes, color VIC TTGGAGCTGTTGGCGT, (SEQ ID NO: 8)
mutated probe, color FAM TTGGAGCTGTTGGCGT.
```

For the G13C mutation of the K-ras gene coding for resistance to Erlotinib and Gefitinib:

```
                                        (SEQ ID NO: 9)
forward primer AGGCCTGCTGAAAATGACTGAATAT, (SEQ ID NO: 10)
reverse primer TCGTCCACAAAATGATTCTGAATTAGCT, (SEQ ID NO: 11)
native probes, color VIC TTGGAGCTGGTTGCGT, (SEQ ID NO: 12)
mutated probe, color FAM TTGGAGCTGGTTGCGT.
```

For the L858R mutation of the EGFR gene coding for increased sensitivity to Erlotinib and Gefitinib:

```
                                        (SEQ ID NO: 13)
forward primer GCAGCATGTCAAGATCACAGATTT, (SEQ ID NO: 14)
reverse primer CCTCCTTCTGCATGGTATTCTTTCT, (SEQ ID NO: 15)
native probes, color VIC CAGTTTGGCCCGCCCA, (SEQ ID NO: 16)
mutated probe, color FAM CAGTTTGGCCCGCCCA.
```

The meanings of "forward", "reverse" and "5' to 3'" are well known to the person skilled in the art. The probes are matched between the two primers and reveal the presence or absence of a mutation because of their associated fluorescence color. The color FAM is a blue and the color VIC is a green. Measuring the intensity of the fluorescence in each of these colors by the PCR apparatus makes it possible to discriminate normal genes, mutated homozygote genes and mutated heterozygote genes. 50 amplification cycles are performed, for example.

In other embodiments, a defined volume of the genetic material, in particular the RNA converted into cDNA by reverse transcription (RT) and amplified, is sampled to detect the level of expression of the gene coding for sensitivity or resistance to the target therapies using pairs of forward and reverse primers and a probe and during a real-time quantitative polymerase chain reaction (PCR), for example with 50 cycles.

In each of the embodiments described above, the filter is preferably produced in polycarbonate with a hydrophilic surface treatment. The use of such a filter improves the retention of the particular cells and reduces the adhesion of other cells or their contents if they have undergone specific lysis.

The filter preferably has a pore diameter centered on a value lower, for example 1 µm lower, than the corresponding value used for the same cells when fixed, i.e. when rendered rigid.

For example, if the diameter of the pores would have been centered on 7.5 µm for fixed cells, here it is centered on a lower value, for example 6.5 µm. Because of the spread of diameters, practically none of the pores has a diameter greater than 7 µm.

For an application of the invention to blood cells, the filter has pores the density of which is between 50 000 and 200 000 pores/cm$^2$ and preferably approximately 100 000 pores/cm$^2$.

Thanks to the use of a polycarbonate filter, the necessary pressure reduction is much lower than in prior art systems, up to four times lower, which prevents deterioration of the cells collected on the filter. Aspiration by a pressure reduction less than or equal to −25 mBar is preferably effected below the filter.

In variants, the filter support 108 or 308 is mechanically connected to said mobile means until application of the force that release the filter support from the mobile means by movement of the compartment toward the culture well or Eppendorf tube. Interchanging the roles of the lower end of the compartment 102 or 302 and the mobile means 110 or 310 so that it is the latter that hold the filter support in or in front of the culture well or Eppendorf tube and the former that releases it on pressing on the upper end of the compartment is an easy adaptation that will be obvious to the person skilled in the art given the above description of embodiments of the invention.

Note that what has been described above for a single compartment 102 or 302 is preferably effected simultaneously for a large number of compartments held together by a common support (not shown).

In some embodiments, the device of the present invention takes the form of a kit including, in an external sachet, two internal sachets of which:
the first includes the assembled device, as shown in FIG. 2A or 6A, and
the second includes the culture well and a circular plate and/or an Eppendorf tube or any other accessory useful for using the device.

Using the present invention makes it possible to avoid risky sampling of cells, for example amniotic fluid cells, at the same time as enabling cell culture, for example for amniocentesis. Moreover, because of the reservoir form of the filter support 108, immunocytochemistry or fluorescent in situ hybridization (FISH) reactions can be produced directly in this support.

In some embodiments (not shown), a ring is inserted into the lower opening of the syringe-shaped compartment and clamped or glued into that compartment. A washer- or ring-shaped filter support or cup is placed in the ring and retains the filter. The microperforated filter is welded under the cup and then inserted with it into the lower end of the syringe-shaped compartment.

Inside the lower part of the compartment is positioned a part with a downwardly oriented conical interior shape. This part bears on the upper surface of the filter support. The lower half of the part has a length greater than or equal to that of the ring. The connection between the compartment and the part thus has a clearance along the axis of the compartment at least equal to the distance between the top of the support and the lower opening of the ring. In this way, when the part is moved axially by a piston inserted into the syringe-shape compartment, it pushes the support until it is released from the ring and consequently from the syringe-shaped compartment. Moreover, when a piston is inserted in the upper opening of the compartment and the top part of the piston is pressed until the piston comes to bear on the conical part, the piston allows air to pass between its external wall and the internal wall of the compartment and its movement therefore does not increase the pressure inside the compartment, which prevents all risk of damaging live cells carried by the filter. It is seen that, thanks to the conical shape of the part, the piston does not bear on the filter and there is therefore no risk of damaging cells retained on the filter. Similarly, the part presses only on the filter support and thus there is no risk of damaging the cells there either.

By pressing further on the top part of the piston in order for it to move the part downward, exploiting the clearance, the part expels the support from the ring and the compartment. The support and the filter then drop into the plate well and/or the culture flask. The stroke of the piston in the compartment, which is limited by a shoulder at the top of the piston, is preferably such that at the end of the stroke, when the shoulder bears on the upper opening of the compartment, the clearance has been entirely taken up by the movement of the part. This prevents all risk of the ring being torn out, with the attendant risk of it dropping onto the filter in the plate well and/or the culture flask.

The invention claimed is:

1. A device for isolating live cells on a filter, comprising:
a filter support fastened to a filter;
a compartment having an upper opening and a lower opening;
a mobile means that is mobile relative to said compartment for pushing the filter support and releasing said support apart from the compartment or the mobile means; and
a removable end-piece, removably fixed and sealed to the compartment, and, when fixed to the compartment, adapted to prohibit the movement of the mobile means relative to the compartment, said movement makes it possible to push and release said filter support.

2. The device according to claim 1, wherein said end-piece has a lower opening that fits onto a reduced-pressure chamber of an aspiration system.

3. The device according to claim 1, wherein said filter support is a washer.

4. The device according to claim 3, wherein said filter support is formed from PVC.

5. The device according to claim 4, wherein said filter support is formed from rigid PVC.

6. The device according to claim 1, wherein said filter support takes a form of an object cover slide.

7. The device according to claim 1, wherein said filter support has dimensions greater than or equal to those of an object cover slide.

8. The device according to claim 1, wherein said filter support has a thickness less than or equal to 0.4 mm.

9. The device according to claim 1, wherein said filter support takes a form of an Eppendorf tube.

10. The device according to claim 9, wherein the filter support includes polycarbonate.

11. The device according to claim 1, wherein the filter support is mechanically connected to said compartment until the mobile means moves relative to said compartment for pushing the filter support and releasing said filter support apart from the compartment or the mobile means.

12. The device according to claim 1, wherein said filter support is mechanically connected to said mobile means until the mobile means moves relative to said compartment for pushing the filter support and releasing said filter support apart from the compartment or the mobile means.

13. The device according to claim 1, wherein the compartment comprises a guide that guides the mobile means when the mobile means moves relative to said compartment for pushing the filter support and releasing said filter support apart from the compartment or the mobile means.

14. The device according to claim 13, wherein the mobile means comprises lugs guided by said guide, said lugs pushing the filter support when the mobile means moves relative to said compartment for pushing the filter support and releasing said filter support apart from the compartment or the mobile means.

15. The device according to claim 1, wherein the compartment has a longitudinal axis and the mobile means moves relative to said compartment parallel to said axis for pushing the filter support and releasing said filter support apart from the compartment or the mobile means.

16. The device according to claim 1, wherein said end piece grips an exterior wall of the compartment, has a tapered lower opening of smaller diameter than a diameter of the compartment, and is placed at the lower opening of the compartment in a sealed sterile and removable fashion.

17. The device according to claim 14, wherein said end-piece has a rotation lock for gripping the lugs of the mobile means in a manner so that the end-piece guarantees that the filter support is held in position during a filtration step.

18. The device according to claim 17, wherein said lugs curve toward each other so that the mobile means, after withdrawal of the end-piece, pushes the filter support to be released from the compartment on movement of the mobile means towards the filter support.

\* \* \* \* \*

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Synthetic Primer

<400> SEQUENCE: 1
aggcctgctg aaaatgactg aatat                                         25

<210> SEQ ID NO 2
<211> LENGTH: 28
<212> TYPE: DNA
<213> ORGANISM: Artificial Sequence
<220> FEATURE:
<223> OTHER INFORMATION: Synthetic Primer

<400> SEQUENCE: 2
tcgtccacaa aatgattctg aattagct                                      28

<210> SEQ ID NO 3
<211> LENGTH: 16
<212> TYPE: DNA
<213> ORGANISM: Artificial Sequence
<220> FEATURE:
<223> OTHER INFORMATION: Synthetic Primer

<400> SEQUENCE: 3
ttggagctgg tggcgt                                                   16

<210> SEQ ID NO 4
<211> LENGTH: 15
<212> TYPE: DNA
<213> ORGANISM: Artificial Sequence
<220> FEATURE:
<223> OTHER INFORMATION: Synthetic Primer

<400> SEQUENCE: 4
tggagctgat ggcgt                                                    15

<210> SEQ ID NO 5
<211> LENGTH: 25
<212> TYPE: DNA
<213> ORGANISM: Artificial Sequence
<220> FEATURE:
<223> OTHER INFORMATION: Synthetic Primer

<400> SEQUENCE: 5
aggcctgctg aaaatgactg aatat                                         25

<210> SEQ ID NO 6
<211> LENGTH: 28
<212> TYPE: DNA
<213> ORGANISM: Artificial Sequence
<220> FEATURE:
```

-continued

```
<223> OTHER INFORMATION: Synthetic Primer

<400> SEQUENCE: 6
tcgtccacaa aatgattctg aattagct                                              28

<210> SEQ ID NO 7
<211> LENGTH: 16
<212> TYPE: DNA
<213> ORGANISM: Artificial Sequence
<220> FEATURE:
<223> OTHER INFORMATION: Synthetic Primer

<400> SEQUENCE: 7
ttggagctgg tggcgt                                                           16

<210> SEQ ID NO 8
<211> LENGTH: 16
<212> TYPE: DNA
<213> ORGANISM: Artificial Sequence
<220> FEATURE:
<223> OTHER INFORMATION: Synthetic Primer

<400> SEQUENCE: 8
ttggagctgt tggcgt                                                           16

<210> SEQ ID NO 9
<211> LENGTH: 25
<212> TYPE: DNA
<213> ORGANISM: Artificial Sequence
<220> FEATURE:
<223> OTHER INFORMATION: Synthetic Primer

<400> SEQUENCE: 9
aggcctgctg aaaatgactg aatat                                                 25

<210> SEQ ID NO 10
<211> LENGTH: 28
<212> TYPE: DNA
<213> ORGANISM: Artificial Sequence
<220> FEATURE:
<223> OTHER INFORMATION: Synthetic Primer

<400> SEQUENCE: 10
tcgtccacaa aatgattctg aattagct                                              28

<210> SEQ ID NO 11
<211> LENGTH: 16
<212> TYPE: DNA
<213> ORGANISM: Artificial Sequence
<220> FEATURE:
<223> OTHER INFORMATION: Synthetic Primer

<400> SEQUENCE: 11
ttggagctgg tggcgt                                                           16

<210> SEQ ID NO 12
<211> LENGTH: 16
<212> TYPE: DNA
<213> ORGANISM: Artificial Sequence
<220> FEATURE:
<223> OTHER INFORMATION: Synthetic Primer

<400> SEQUENCE: 12
ttggagctgg ttgcgt                                                           16
```

-continued

```
<210> SEQ ID NO 13
<211> LENGTH: 24
<212> TYPE: DNA
<213> ORGANISM: Artificial Sequence
<220> FEATURE:
<223> OTHER INFORMATION: Synthetic Primer

<400> SEQUENCE: 13
gcagcatgtc aagatcacag attt                                          24

<210> SEQ ID NO 14
<211> LENGTH: 25
<212> TYPE: DNA
<213> ORGANISM: Artificial Sequence
<220> FEATURE:
<223> OTHER INFORMATION: Synthetic Primer

<400> SEQUENCE: 14
cctccttctg catggtattc tttct                                         25

<210> SEQ ID NO 15
<211> LENGTH: 16
<212> TYPE: DNA
<213> ORGANISM: Artificial Sequence
<220> FEATURE:
<223> OTHER INFORMATION: Synthetic Primer

<400> SEQUENCE: 15
cagtttggcc agccca                                                   16

<210> SEQ ID NO 16
<211> LENGTH: 16
<212> TYPE: DNA
<213> ORGANISM: Artificial Sequence
<220> FEATURE:
<223> OTHER INFORMATION: Synthetic Primer

<400> SEQUENCE: 16
cagtttggcc cgccca                                                   16
```